United States Patent [19]

Binaris et al.

[11] 4,204,438

[45] May 27, 1980

[54] TATTOOING DEVICE

[76] Inventors: Christopher Binaris, 157 Brightwood Ave., Westfield, N.J. 07090; Patricia S. Volz, 74 Hoyt St., Darien, Conn. 06820; Joseph Ohidy, 828 4th Ave., Westfield, N.J. 07090

[21] Appl. No.: 911,938

[22] Filed: Jun. 2, 1978

[51] Int. Cl.² .............................................. B43K 5/00
[52] U.S. Cl. .......................................... 81/9.22; 30/362
[58] Field of Search .................... 81/9.22; 30/362, 366

[56] References Cited

U.S. PATENT DOCUMENTS

| | | | |
|---|---|---|---|
| 464,801 | 12/1891 | O'Reilly | 81/9.22 |
| 485,767 | 11/1892 | Lewis | 81/9.22 |
| 516,212 | 3/1894 | Lewis | 81/9.22 |
| 768,413 | 8/1904 | Wagner | 81/9.22 |
| 839,888 | 1/1907 | Pryor | 81/9.22 |
| 990,786 | 4/1911 | Selig | 30/362 |
| 1,724,812 | 8/1929 | Waters | 81/9.22 |
| 2,307,424 | 1/1943 | Savage | 30/366 |
| 4,031,783 | 6/1977 | Paul et al. | 81/9.22 |

*Primary Examiner*—James G. Smith

*Attorney, Agent, or Firm*—Lerner, David, Littenberg & Samuel

[57] ABSTRACT

A tattooing device is provided which includes a motor housing and a needle housing secured thereto. A motor and an eccentric drive structure driven by the motor are mounted in the motor housing. In addition, a needle shaft and tattooing needle are mounted for reciprocation in the needle housing and are driven to reciprocate by the eccentric drive structure in the motor housing. The needle housing has an opening at the lower end thereof through which the tattooing needle reciprocates, and a silicone rubber bushing is mounted in the needle housing and is provided with an opening through which the needle extends. The diameter of the bushing opening is less than the diameter of the opening in the lower end of the needle housing so that the bushing operates to constrain transverse movement of the reciprocating needle and thereby reduces noise, ink splatter, the tearing of skin, and improves line clarity. In a preferred embodiment, the motor housing is provided with a mercury switch for energizing and de-energizing the motor so that the tattooing device can be operated with only one hand.

8 Claims, 12 Drawing Figures

TATTOOING DEVICE

FIELD OF THE INVENTION

The present invention relates generally to tattooing devices, and specifically to an improved tattooing device which includes novel features to substantially reduce noise, ink splatter, the tearing of skin, and also improves line clarity.

BACKGROUND OF THE INVENTION

Tattooing devices are well known in the prior art, including tattooing devices for performing a tattoo on an animal. Typically, such tattooing devices include a motor housing and a needle housing secured thereto, with the motor housing having an eccentic drive structure mounted therein, and with the needle housing having a needle shaft and a tattooing needle mounted therein to be reciprocated by the eccentric drive structure. Although such tattooing devices are generally satisfactory, there have been a number of problems and drawbacks experienced with these devices which could be improved upon. For example, such devices are extremely noisy and when performing a tattoo on an animal, the loud noise actually frightens the animal and makes it restless, so that it is much more difficult to perform the tattoo. It has been found that this noise is caused by a number of factors, including the manner in which the motor is mounted, lateral or transverse movement and play in the eccentric drive structure, and transverse movement of the reciprocating needle causing it to engage the sidewalls of the needle housing which creates additional noise. Accordingly, it would be desirable to provide a tattooing device which substantially reduces such noise and provides a quieter operation.

In addition, in such prior art tattooing devices, the transverse movement of the reciprocating needle also causes tearing of the skin during the performance of the tattoo. Of course, such skin tearing is painful, and it would also be beneficial if this problem could be eliminated or substantially reduced. Also, the transverse movement and/or play in the reciprocating needle also causes the splattering of ink during the performance of the tattoo and also blurs the tattoo lines which are made so that there is a lack of line clarity in the tattoo. Accordingly, it would also be desirable to provide an improved tattooing device which has improved line clarity and which does not splatter ink during the performance of the tattoo.

Broadly, it is an object of the present invention to provide an improved tattooing device which overcomes one or more of the aforesaid problems. Specifically, it is within the contemplation of the present invention to provide a tattooing device which is constructed so as to substantially reduce transverse movement of the reciprocating tattoo needle and thereby substantially reduce noise, ink splatter, and the tearing of skin while performing the tattoo, as well as improving line clarity of the tattoo.

It is a further object of the present invention to provide an improved tattooing device which includes novel features to prevent or substantially reduce transverse movement of the reciprocating needle and the problems caused thereby.

It is a still further object of the present invention to provide an improved tattooing device which can be turned on and off while being held with only one hand during the performance of a tattoo.

SUMMARY OF THE INVENTION

Briefly, in accordance with the principles of the present invention, an improved tattooing device is provided which includes a motor housing and a needle housing secured thereto. A motor and an eccentric drive structure for driving the motor are mounted in the motor housing, and a needle shaft and a tattooing needle are mounted for reciprocation in the needle housing and are driven to reciprocate by the eccentric drive structure in the motor housing. At the lower end of the needle housing, there is an opening through which the tattooing needle reciprocates, and a silicone rubber bushing having an internal opening extending therethrough is mounted at the lower portion of the needle housing so that the tattooing needle extends therethrough.

Advantageously, as a result of the present invention, the diameter of the internal opening of the bushing is less than the diameter of the opening at the lower end of the needle housing so that the silicone rubber bushing operates to limit the transverse movement of the reciprocating needle. In this manner, the lower end of the needle, while reciprocating, is substantially prevented from engaging the walls of the lower end of the needle housing, since the transverse movement of the reciprocating needle is limited by the silicone bushing. As a result, the improved tattooing device of the present invention produces less noise, less ink splatter, and also reduces the tearing of skin while performing the tattoo, and also improves the line clarity of the tattoo which is performed.

As a further advantage of the present invention, the eccentric drive structure has been improved so as to substantially reduce transverse movement of the reciprocating needle at its upper end. Also, the motor mounting has also been modified to include a recess form therein so that the motor is mounted for quiet operation and reduced vibration.

As a still further advantage of the present invention and in order to further reduce noise in the operation of the tattooing device, the needle housing and needle shaft have been modified to increase the space between these elements and to thereby prevent the needle shaft from engaging the wall of the needle housing to further reduce noise.

As a still further advantage, in one embodiment of the present invention, the motor housing has been provided with a mercury switch so that the motor can be energized and de-energized with only one hand while performing a tattoo.

BRIEF DESCRIPTION OF THE DRAWINGS

Further objects, features, and advantages of the present invention will become apparent upon the consideration of the following detailed description of a presently-preferred embodiment when taken in conjunction with the accompanying drawings, wherein.

DETAILED DISCUSSION OF PREFERRED EMBODIMENTS OF THE INVENTION

Figure 1:
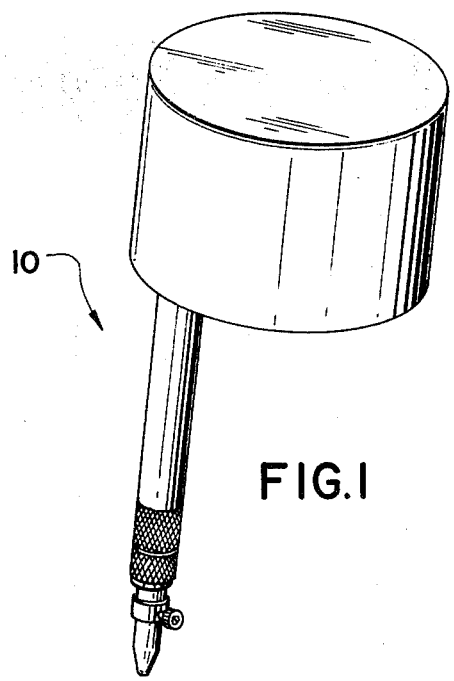
FIG. 1 is a perspective view of the improved tattooing device of the present invention.
Figure 2:
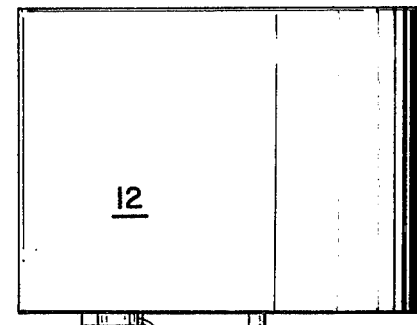
FIG. 2 is a side elevational view of the improved tattooing device.
Figure 3:
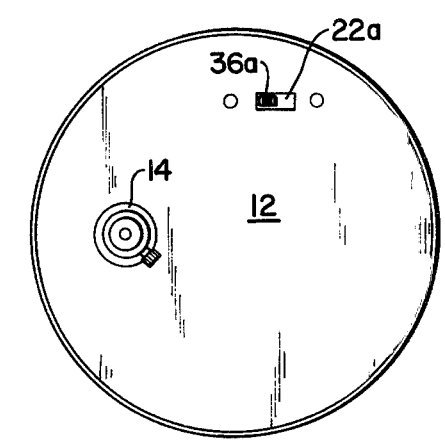
FIG. 3 is a bottom view of the improved tattooing device.

Referring now to FIGS. 1 to 3 of the drawings, there is shown the improved tattooing device of the present invention, generally designated by the reference numeral 10, which includes a motor housing 12 and a needle housing 14 secured thereto at 16 by a suitable threaded connection.

Referring now specifically to FIGS. 4 to 7, the interior of the motor housing 12 is illustrated. It includes a removable cylindrical cover 20 which is removably snap fit on a base member 22. A mounting member 24, including three legs 24a, 24b, and 24c, is secured to the base member 22. Mounted on the upper surface of leg 24c is a battery compartment 26 for receiving two 1.5 volt batteries 28, 30. As shown most clearly in FIG. 5, a motor 32 is mounted on the lower surface of leg 24c in a recess 24d formed therein. In this manner, by having motor 32 secured within recess 24d, vibrations of the motor 32 are reduced and quiet operation is enhanced.

Figure 4:
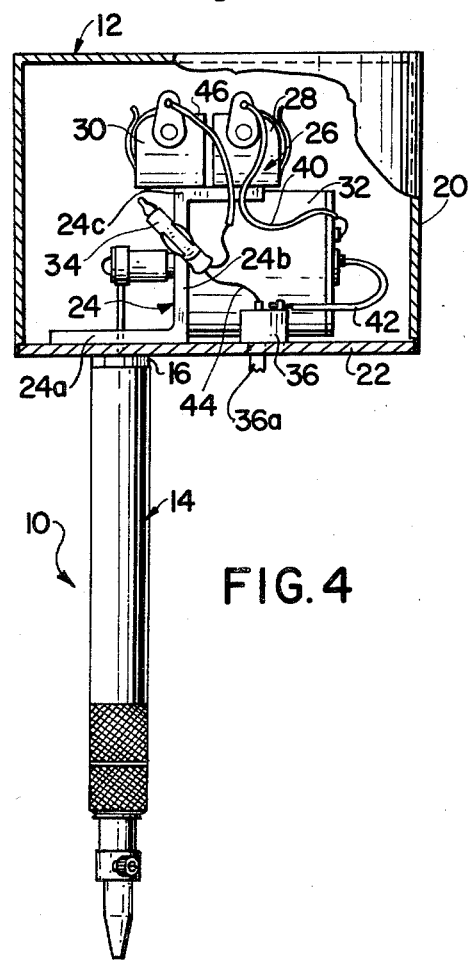
FIG. 4 is an elevational view of the improved tattooing device, with the motor housing partially removed to illustrate the interior elements thereof.
Figure 5:
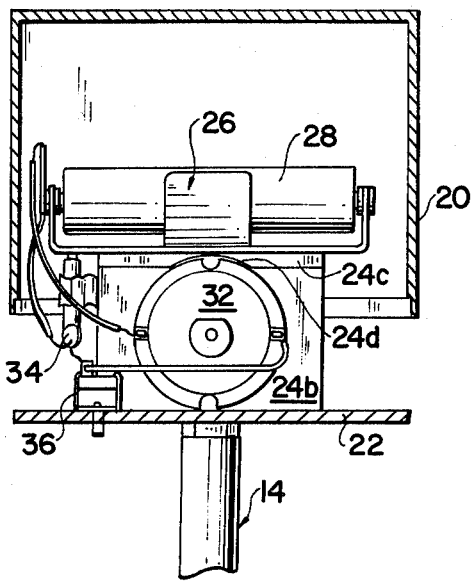
FIG. 5 is an elevational view of the motor housing, with the cover partially removed.
Figure 6:
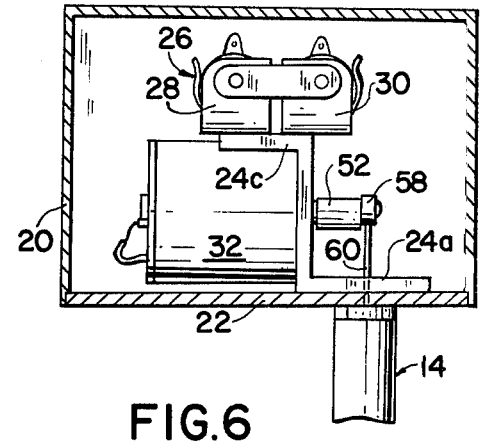
FIG. 6 is an elevational view of the motor housing taken in a first direction.
Figure 7:
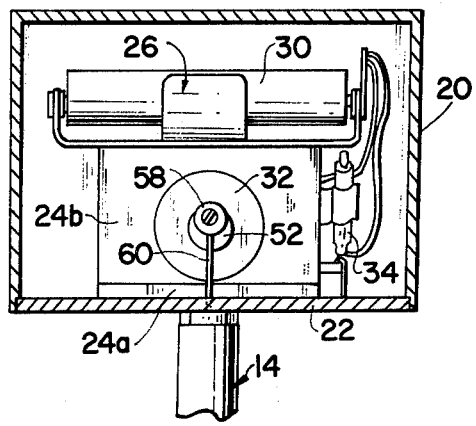
FIG. 7 is an elevational view of the motor housing taken in a second direction.

As also shown in FIGS. 4, 5, and 7, a mercury switch 34 is secured to vertical leg 24b of mounting member 24. In addition, a manually-operated switch 36 is secured to base member 22, with its actuating member 36a extending through an opening 22a formed in base member 22, as shown most clearly in FIG. 3.

As will be seen in FIG. 4, all of the electrical elements are connected in series for operation of the tattooing device. Batteries 28 and 30 are connected by a lead 40 to motor 32, and motor 32 is in turn connected by a lead 42 to manual switch 36, which is connected by a lead 44 to mercury switch 34. To complete the circuit, mercury switch 34 is connected by lead 46 to one end of battery 30. As will be understood, when the tattooing device is in its upright position, mercury switch 34 does not break the circuit so that actuation of switch member 36 will turn motor 32 on and off. However, once switch 36 is in its on position, when the tattooing device 10 is tilted to an approximately 60° angle, the mercury switch is operated to break the circuit and turn off motor 32. In this manner, the user of the tattooing device 10 can hold needle housing 14 with one hand and perform a tattoo, and when it is desired to de-energize the motor, it is only necessary to tilt the hand and tattooing device to turn off the motor 32. Advantageously, the user has the other hand free to perform other functions, such as holding the animal in place so that it does not move.

Figure 8:
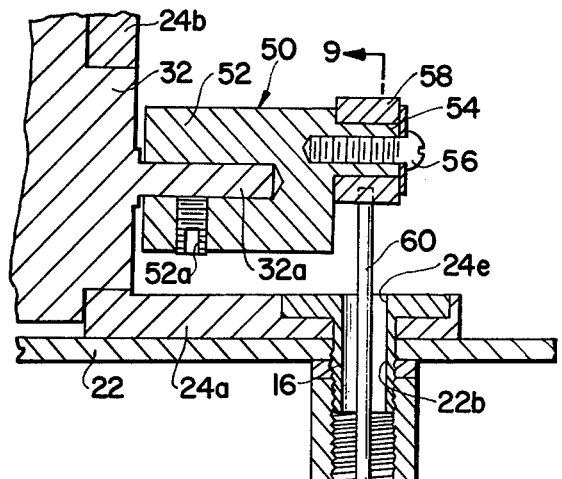
FIG. 8 is a sectional view of the eccentric drive structure of the improved tattooing device of the present invention.
Figure 9:
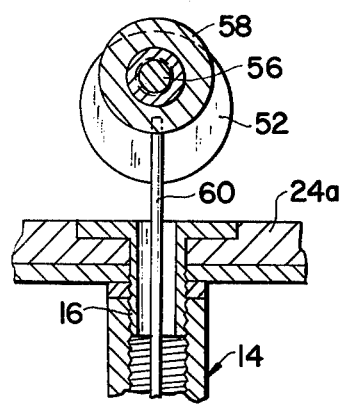
FIG. 9 is a sectional view, taken on line 9–9 of FIG. 8, to illustrate the additional details of the eccentric drive structure.

Turning now to FIG. 8, the eccentric drive structure 50 of the present invention is illustrated in detail. The motor 32 is provided with an output shaft 32a, on which is mounted a boss 52 which is secured to motor shaft 32a by a suitable set screw 52a or the like. The right end of boss 52 is provided with an integral driving cam 54 extending from the end thereof and which is provided with a threaded hole for receiving a screw 56. The needle shaft 60 is provided at the upper end thereof with a head 58 which surrounds driving cam 54 and is securely fastened thereto by screw and washer 56. As a result of this eccentric drive structure 50, motor shaft 32a operates to rotate boss 52 and driving cam 54 so that needle shaft 60 is reciprocated at high speed. In addition, as a result of the manner in which the elements of eccentric drive structure 50 are secured together, transverse movement of the reciprocating needle shaft 60 is substantially limited.

As will be noted, needle shaft 60 extends through an opening 24e formed in lower leg 24a and also extends through an opening 22b formed in base member 22. As explained above, needle housing 14 is threadedly secured to a member 16 extending from base member 22 of the motor housing 12.

Figure 10:
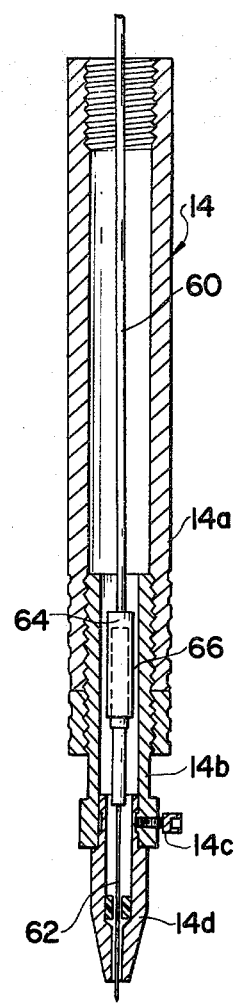
FIG. 10 is a sectional view, in elevation, of the needle housing, with the needle shaft and tattooing needle mounted therein for reciprocation.
Figure 11:
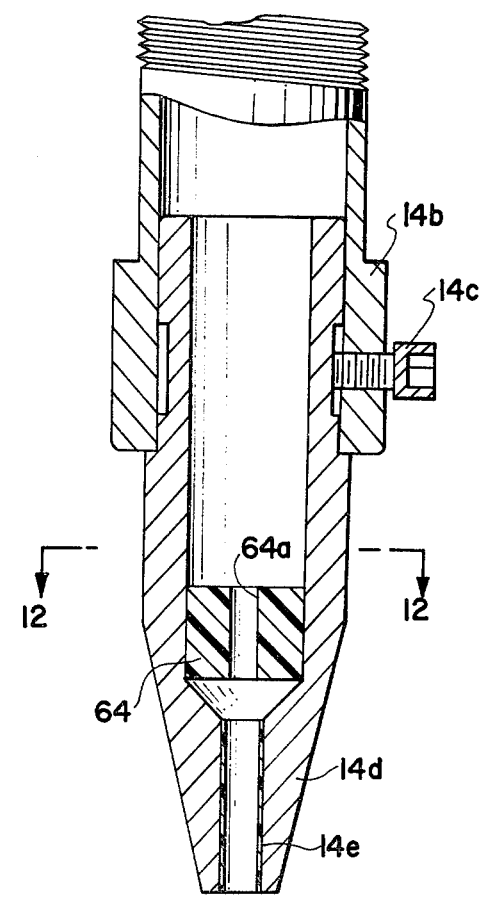
FIG. 11 is an enlarged sectional view of the lower end of the needle housing illustrating the silicone rubber bushing mounted therein.
Figure 12:
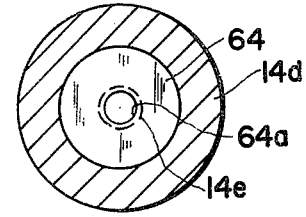
FIG. 12 is a sectional view, taken on line 12—12 of FIG. 11 to illustrate the smaller opening of the bushing as compared to the opening at the lower end of the needle housing.

Turning now to FIGS. 10, 11, and 12, the details of the needle housing 14 are illustrated. As shown, needle housing 14 includes an upper section 14a threadedly secured to a middle section 14b which is in turn secured by a set screw 14c to a bottom section 14d. In this manner, by the use of set screw 14c, bottom section 14d is adjustable with respect to middle section 14b. As will also be noted, needle shaft 60 has a suitable tattooing needle 62 secured thereto. Preferably, tattooing needle 62 is a four-part stainless steel needle.

As shown most clearly in FIGS. 11 and 12, bottom section 14d includes an opening 14e at the lowermost end thereof through which tattooing needle 62 extends. In addition, mounted internally within bottom section 14d is a silicone rubber bushing 64 having an internal opening 64a through which tattooing needle 62 extends. As will be seen most clearly in FIG. 12, the diameter of opening 64a of bushing 64 is smaller than the diameter of opening 14e. As a result, during reciprocation of tattooing needle 62, any transverse movement of the reciprocating needle will cause it to engage the internal walls of bushing 64 without engaging the walls of opening 14e. As a result, since bushing 64 is formed of silicone rubber, whereas the walls of opening 14e are formed of metal, a quieter operation is provided. In addition, silicone bushing 64 also operates to prevent needle 62 and needle shaft 60 from engaging the interior sidewalls of upper and middle sections 14a, 14b of needle housing 14. This also reduces the noise produced in operating the tattooing device of the present invention.

It is also noted that the diameter of the lowermost portion 64 of needle shaft 60 has been reduced in diameter, and the thickness of the overlapping wall sections of upper and middle sections 14a, 14b has also been reduced so as to increase the space 66 between needle shaft section 64 and the interior wall of middle section 14b to thereby further reduce engagement between needle shaft 64 and needle housing wall 14b which further operates to reduce the noise produced when operating the tattooing device of the present invention.

In view of the foregoing, it will be appreciated that there has been provided in accordance with the present invention a number of novel features which cooperate to substantially reduce the amount of noise produced when using the tattooing device of the present invention. This is of great benefit, especially when the tattooing device is used for tattooing animals, since they are afraid and become restless when subject to noisy instruments. These novel features for reducing noise include a quieter motor 32 and a more secure mounting of the motor in recess 24d. In addition, the eccentric drive structure 50 at the upper end of needle shaft 60 also cooperates with silicone bushing 64 at the lower end of needle shaft 60 to reduce or substantially eliminate engagement of the needle shaft with the walls of the needle housing to thereby further reduce noise. Further, as explained above, the space 66 between needle shaft section 64 and needle housing section 14b has been increased to prevent the needle shaft from engaging the wall of the needle housing to thereby further reduce noise.

It will also be appreciated that as a result of the present invention, transverse movement or transverse play of the reciprocating needle shaft 60 and tattooing needle 62 has been substantially reduced. Advantageously, the reduction of such transverse movement provides the benefit of eliminating the tearing of skin during the tattooing operation, as well as reducing or eliminating the amount of ink splatter. As a result, the line clarity of the tattoo made by the tattooing device of the present invention is also improved. The novel features of the present invention which reduce such transverse movement or play of the reciprocating needle shaft 60 and needle 62 include the novel eccentric drive structure 50, as well as the small internal diameter 64a of a silicone rubber bushing 64.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A tattooing device for performing a tattoo, comprising:

a motor housing and a needle housing secured to said motor housing, said motor housing having mounted therein a motor and an eccentric drive structure driven by said motor, a needle shaft and tattooing needle mounted for reciprocation in said needle housing and driven to reciprocate by said eccentric drive structure, said needle housing having an opening at the lower end thereof through which said tattooing needle reciprocates, and a bushing formed of noise reducing material mounted in the bottom section of said needle housing and having an internal opening through which said tattooing needle extends, the internal diameter of said bushing opening being less than the internal diameter of said needle housing opening so that said bushing operates to constrain transverse movement of said reciprocating needle and thereby reduces noise, ink splatter, and the tearing of skin and improves the line clarity of the tattoo produced.

2. A tattooing device in accordance with claim 1, wherein said eccentric drive structure includes means for reducing transverse movement of said reciprocating tattoo needle.

3. A tattooing device in accordance with claim 2, wherein said reducing means includes a boss mounted on the output shaft of said motor, said boss including an integral cam extending therefrom, said cam being connected to the head of said needle shaft to drive said needle shaft to reciprocate in said needle housing, said boss and said head being securely fastened to reduce transverse movement of said reciprocating needle shaft.

4. A tattooing device in accordance with claims 1, 2, or 3, wherein said motor housing includes a mercury switch mounted therein for energizing and de-energizing said motor.

5. A tattooing device in accordance with claims 1, 2, or 3, wherein said motor housing includes a mounting member having a recess formed therein, in which said motor is securely mounted to reduce motor vibration and to enhance quiet operation.

6. A tattooing device in accordance with claims 1 or 2, further including means for preventing said needle shaft from engaging the interior walls of said needle housing by increasing the space therebetween in order to reduce noise.

7. A tattooing device in accordance with claim 6, wherein said means for preventing engagement includes a needle housing wall which is relatively thin and a needle shaft having a relatively small diameter so as to increase the space between said needle housing wall and the needle shaft to thereby prevent engagement between said elements to reduce noise.

8. A tattooing device in accordance with claims 1 or 2, wherein said bushing is formed of silicone rubber.

* * * * *